United States Patent [19]
Ikematsu et al.

[11] Patent Number: 5,378,342
[45] Date of Patent: Jan. 3, 1995

[54] NEURAL MODELING DEVICE
[75] Inventors: Mineo Ikematsu, Tsuchiura; Yukihiro Sugiyama; Masahiro Iseki, both of Tsukuba, all of Japan
[73] Assignee: Sanyo Electric Co., Ltd., Osaka, Japan
[21] Appl. No.: 37,030
[22] Filed: Mar. 25, 1993
[30] Foreign Application Priority Data Mar. 26, 1992 [JP] Japan .................................. 4-068367
[51] Int. Cl.$^6$ ............................................. G01N 27/26
[52] U.S. Cl. .................................... 204/403; 204/418; 422/82.01; 436/151; 436/806
[58] Field of Search ....................... 204/403, 252, 418; 422/82.01; 436/179, 151, 806

[56] References Cited

U.S. PATENT DOCUMENTS 5,041,224 8/1991 Ohyama et al. ................. 210/500.27

FOREIGN PATENT DOCUMENTS 2247894 3/1990 Japan .
396997 11/1992 Japan .
3129153 12/1992 Japan .

OTHER PUBLICATIONS

U.S. Statutory Invention Registration H201 to Yager, published Jan. 6, 1987 "biosensous from membrane proteins reconstituted in polymerized lipid bilayers".
Yoshikawa, Kenichi, "Artificial Neuromembrane", Surface, vol. 2, No. 11 (1988).
Toko, et al., "Phase Transition and Electric Oscillation . . . ", Membrane, 12(1), pp. 12–21 (1987).
Hirata, et al., "Fatty Membrane", Biophysics, vol. 26, No. 6 (1986).
Hamamoto, et al., "The Measurement of Ion Channels . . . ", Cytological Engineering, vol. 7, No. 1 (1988).
Bamberg, E., et al., "Transmembraneous incorporation . . . in planar lipid bilayers", Proc. Natl. Acad. Sci. USA, vol. 78, No. 12, pp.7502–7506, Dec. 1981.
Andersen, O. S., "Gramicidin Channels", Annual Rev. Physiol. 1984, vol. 46, pp. 531–548, (1984).
Bayley, H., et al. "Delipidation, Renaturation, And Reconstitution of Bacteriohodopsin", Methods in Enzymology, vol. 88, pp. 74–81 (1982).
Duschl, A., et al., "Functional Reconstitution of Halorhodopsin", Journal of Biological Chemistry, vol. 263, No. 32, pp. 17016–17022, Nov. 15, 1988.
Muneyuki, E., et al., "Heterogeneous hydrolysis of . . . Atp . . . from . . . Coli", Biochimica et Biophysica Acta, 1058 (1991) pp. 304–311.
Dempsey, C. E., "The actions of melittin on membranes", Biochimica et Biophysica Acta, B. 1031 (1990) pp. 143–161.
Gordon, L. G. M., et al., "Kinetics And Stability of . . . Lipid Bilayers", Biochima et Biophysica Acta, vol. 436 (1976) pp. 541–556.
Drachev, Lei A., "Lipid-Impregnated Filters . . . " Analytical Biochemistry., vol. 96, pp. 250–262 (1979).
Block, M. C., et al. "Reconstitution of Baceriohodopsin . . . ", FEBS letters, vol. 76, No. 1, Apr., 1977, pp. 45–50.
Wolley, G. Andrew, et al., "Model Ion Channels . . . " J. Membrane Biol., vol. 129, pp. 109–136 (1991).
Tien, H. Ti, "Bilayer Lipid Membraners (BLM) theory and practice", Marcel Dekker, Inc., New York, 1974.

Primary Examiner—T. Tung
Assistant Examiner—Brendan Mee
Attorney, Agent, or Firm—Spensley Horn Jubas & Lubitz

[57] ABSTRACT

A neural modeling device comprising an electrolyte, a lipid or lipid-impregnated membrane which is situated in the electrolyte and in which an ion pump and an ion channel are buried, and an electrode for transmitting a potential of the lipid or lipid-impregnated membrane as an electrical signal. The ion pump actively transports selected ions in the electrolyte through the membrane from one side to the other side in response to an external stimulus such as light irradiation. When the difference in potential between the opposite sides of the membrane reaches a threshold, the ion channel opens to passively transport selected ions in a direction reverse to the ion transporting direction of the ion pump. When this device is exposed to light, the ion pump actively transports ions to generate a potential in the lipid or lipid-impregnated membrane. Upon detection of this potential, the ion channel opens to eliminate the potential, and then another potential will be generated again by the active transportation of the ion pump. Thus it is possible to generate an oscillating electrical signal by an external stimulus such as light irradiation.

10 Claims, 8 Drawing Sheets compartment X    compartment Y

(a)

(b)

NEURAL MODELING DEVICE

BACKGROUND OF THE INVENTION

1. Field of the Invention

This invention relates to a neural modeling device for generating a non-linear vibrating signal which is to be a factor of information transmission using an oscillating electrical signal in neural cells of an organism.

2. Description of the Related Art

In information processing in a living body, an ignition of a nerve system is the source of information transmission and is thought of as a vibration produced by a function of protein in an organism membrane. This vibrating signal varies diversely, depending on the external stimulus, to transmit the stimulus information to a central nerve.

As a means for obtaining this vibration artificially using an organic material, there is currently known a modeling device for obtaining a vibrating signal from a lipid membrane in an electrolyte. This is an electrical vibration to be produced by a fluctuation of a lipid molecule. This prior art is exemplified by "Surface" by Yoshikawa, Vol. 26, No. 11, 1988 and "Membrane" by Toko and Yamafuji, Vol. 12, No. 1, 1987.

This prior art, however, is totally silent about the existence of protein in the membrane to generate the electrical oscillation. Consequently, it was difficult to generate a particular mode of vibration by an input from an external source, namely, it was difficult to control the vibration, so this prior modeling device cannot be regarded as a nerve modeling device.

SUMMARY OF THE INVENTION

It is therefore an object of this invention to provide a neural modeling device in the form of a so-called biomembrane model whose basic structure is a lipid membrane in which protein or polypeptide allowing transportation or passage of various ions are impregnated, giving a vibration varying diversely commensurate with an external stimulus such as light irradiation or a chemical substance addition.

According to the invention, there is provided a neural modeling device for generating an oscillating electrical signal, comprising: an electrolyte stored in a container; a lipid or lipid-impregnated membrane situated so as to divide the electrolyte; electrodes for carrying a potential of the lipid or lipid-impregnated membrane as an electrical signal; an ion pump buried in the lipid or lipid-impregnated membrane to provide active-transport of ions in the electrolyte through the lipid or lipid-impregnated membrane from one side to the other side by an external stimulus; and an ion channel buried in the electrolyte to enable passive-transport of ions of the same sign as that of the ions actively transported by the ion pump.

With this arrangement, by combining the ion pump, which is buried in the lipid or lipid-impregnated membrane so as to divide the electrolyte, thus serving to increase the membrane potential difference by the ion transportation in response to an external stimulus, with the ion channel, which opens, depending on this membrane potential difference, to reduce it, it is possible to obtain a phenomenon in which the membrane potential difference fluctuates with a constant period, and hence it is possible to obtain this phenomenon as an oscillating electrical signal from the electrode.

In this modeling device, the ion pump actively transports selected ions in the electrolyte through the membrane from one side to the other in response to an external stimulus such as light irradiation, while the ion channel opens, when the difference in membrane potential reaches a threshold, and hence passively transports selected ions in a direction opposite to the direction of ion transportation by the ion pump. Therefore, when this device is exposed to light, the ion pump actively transports ions to produce a membrane potential difference across the lipid or lipid-impregnated membrane. Upon detection of this membrane potential difference, the ion channel opens to remove the membrane potential, whereupon a membrane potential will be created again as ions are actively transported by the ion pump. The foregoing procedures are repeated. Based on such principles, it is possible to produce an oscillating electrical signal simply by giving an external stimulus such as light irradiation.

DETAILED DESCRIPTION

The principles of generation of an oscillating electrical signal by a neural modeling device of this invention will now be described.

Figure 1:
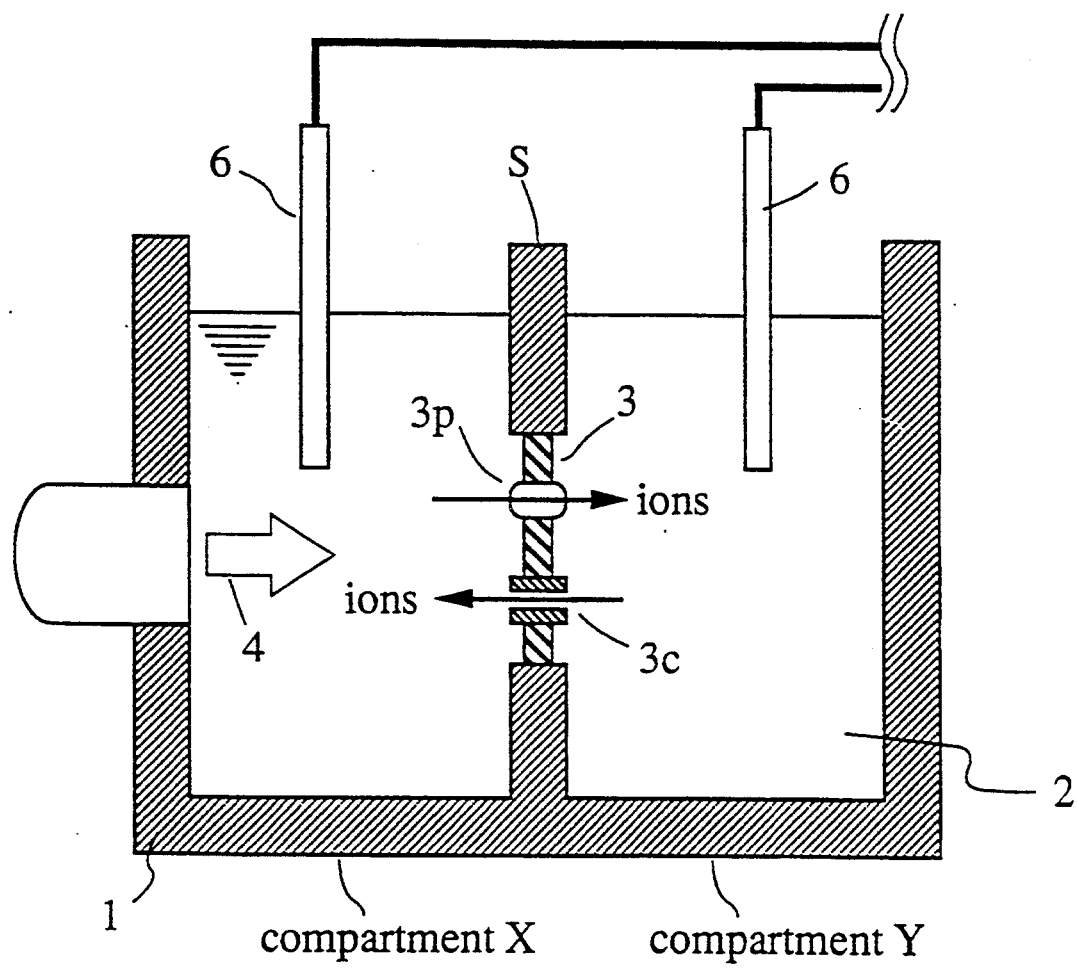
FIG. 1 is a diagram illustrating the operative principles of a neural modeling device according to this invention.

The neural modeling device of the invention, as shown in FIG. 1, comprises an electrolyte 2, a lipid membrane 3 and electrodes 6. The ion pump 3p and the ion channel 3c are buried in the lipid membrane 3, and the lipid membrane 3 is mounted in a partition wall S of a cell 1 dividing the electrolyte 2 into compartments X and Y. The ion pump 3p transports ions from the compartment X to the compartment Y in response to an external stimulus 4 such as light irradiation from a light source, and the transported ions and those having a sign similar thereto pass through the lipid membrane 3 from the compartment Y to the compartment X via the ion channel 3c that has opened due to the change of membrane potential. An oscillating electrical signal is obtained as the electrode 6 captures a membrane potential varying due to this ion movement.

First Embodiment

Figure 2:
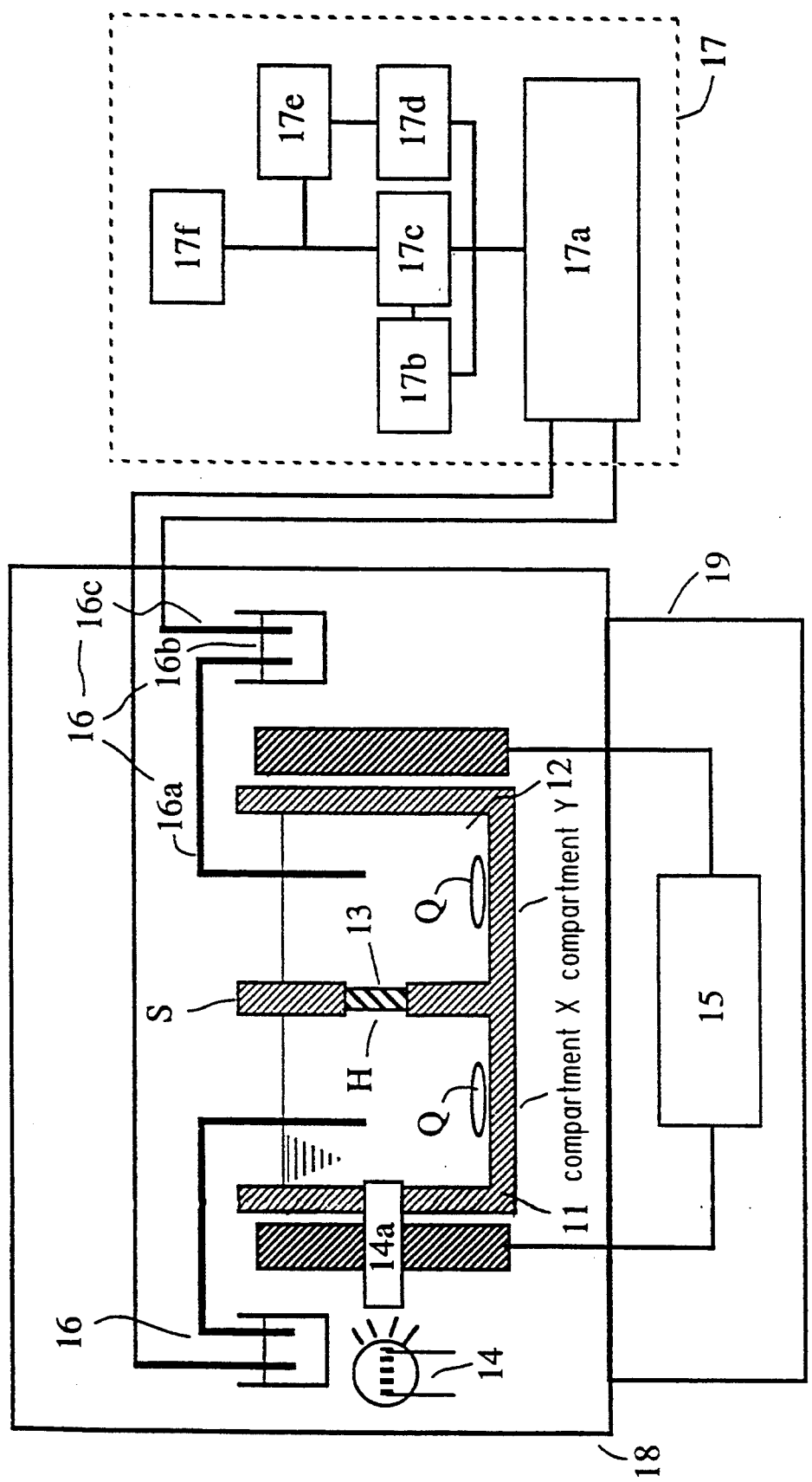
FIG. 2 is a diagram showing a neural modeling device according to a first embodiment of the invention.

FIG. 2 shows a first embodiment of this invention in the form of a popular measuring system for characterization of a lipid bilayer membrane, in which an electrolyte 12 in a cell 11 is divided into compartments X and Y by a partition wall S and is stirred by stirrers Q, In this embodiment, the cell 11 is partitioned off into two compartments (i.e., compartments X and Y) each of 1.5 ml volume by the partition wall S having a thickness of 25 $\mu$m. The partition wall S has a hole H having a diameter of about 200 $\mu$m, in which a lipid bilayer membrane 13 is formed. An ion pump and an ion channel are buried in the lipid blayer membrane 13. Further the cell 11 is provided with a light source 14 and a light guide 14a for irradiating the lipid bilayer membrane 13 with light. The cell 11 and the partition wall S should comprise preferably a substance resistant against an organic solvent; fluorine resin is used in this embodiment. The temperature of the electrolyte 12 in the cell 11 is controlled by a circulator 15. In both the compartment X and the compartment Y are placed, an electrode 16 composed of a salt bridge 16a, 1 mol/l of KCl solution 16b, and silver/silver chloride electrode 16c. An oscillating electrical signal obtained from the electrode 16 is send to an information processing unit 17 composed of a patch-clamp amplifier 17a, an oscilloscope 17b, a filter 17c, a tape recorder 17d, a chart recorder 17e, and a computer 17f. According to the foregoing lipid bilayer membrane measuring system, the light source 14 is provided outside the shield box 18, and the light is lead into the cell 11 through the heat absorption filter 14b and via the light-guide 14a. Thus, the heat absorption filter 14b absorbs heat and allows only the light to pass, thus preventing heat diffusion, while the light diffusion is also prevented by providing the light-guide 14a for leading the light directly to the cell. In this embodiment, light radiation takes place from the side of the compartment X.

[Formation of Lipid Bilayer Membrane]

The formation of the lipid bilayer membrane 13 will now be described. A lipid bilayer membrane is formed by reconstitution of lipid molecules with the folding method (as described, for example, in "Biophysics" by Hirata and Ohno, Vol. 26, No. 6, 1986 and "Cytological Engineering" by Hamamoto et al., Vol. 7, No. 1, 1988).

The reconstitution of an ion pump and an ion channel into the lipid bilayer membrane has currently been realized by simultaneous spreading of lipid molecules or by direct addition of protein reconstituted in a liposome or solubilized protein (described in for example, "Proceedings of National Academy of Science, U.S.A." by E. Bamberg et al., Vol. 78, No. 12, 1981). In this embodiment, the latter method is used.

FIGS. 3(a) through 3(f) show sequential steps of formation of a lipid bilayer membrane with the folding method and those of reconstitution of the ion pump and the ion channel into a lipid bilayer membrane. Reference numeral 21 designates a fluoric resin cell partitioned into two 1.5 ml compartments (i.e., compartments X and Y) by a partition wall S having a hole H of about 200 $\mu$m in diameter. 25a and 25b designate tubes for injecting a buffer solution into the cell 21.

Figure 3:
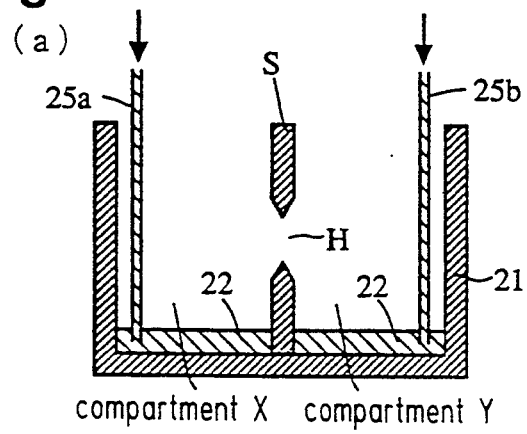
FIGS. 3(a) through 3(f) are cross-sectional views showing various steps of a method for forming a lipid bilayer membrane used in the neural modeling device of the first embodiment.
Figure 3:
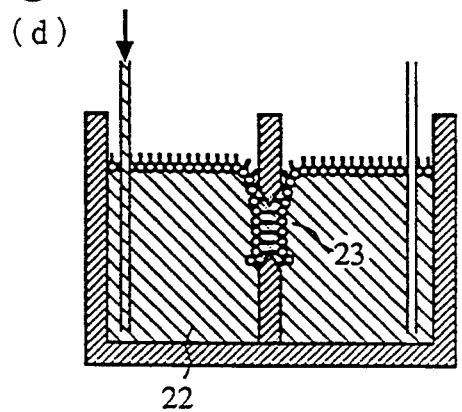
Figure 3:
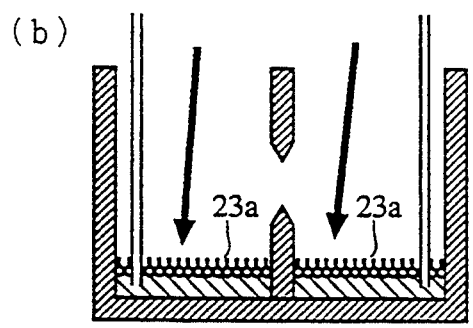
Figure 3:
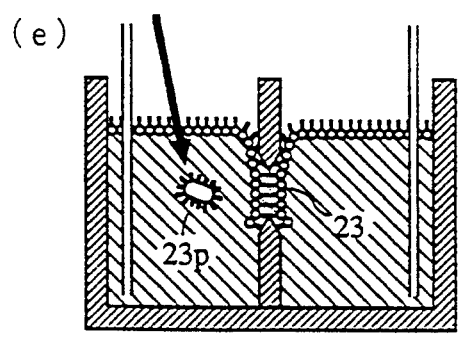
Figure 3:
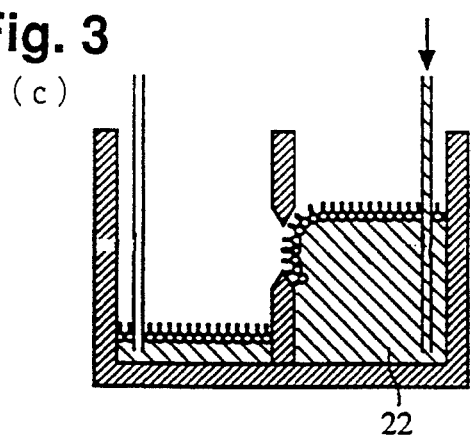
Figure 3:
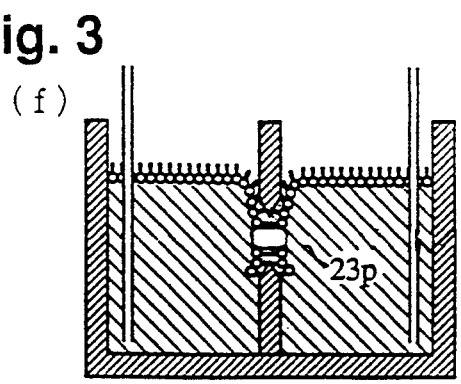

In the first step, as shown in FIG. 3(a), the buffer solution 22 is put into both the compartments X and Y of the cell 21 in such a manner that their respective levels are below the hole H. In this embodiment, the buffer solution is composed of 100 mmol/l of sodium cloride, 20 mmol/l of trismaleate (pH 7.2) and 2 mmol/l of $MgCl_2$.

In the second step, as shown in FIG. 3(b), a lipid solution is spread over the liquid surface of the buffer solution 22. In this embodiment, the lipid solution is 15 $\mu$l of soybean lecithin hexane solution of 10 mg/ml . The spread lipid solution is left to stand for about 5 minutes to volatilize hexane so that a lipid molecule spread layer 23a is formed on the liquid surface of the buffer solution 22.

In the third step, as shown in FIG. 3(c), more buffer solution is injected under the liquid surface of the buffer solution 22 (under the lipid molecule spread layer 23a) in each of the compartments X and Y via respective tubes 25a and 25b to raise the respective liquid surfaces gradually. As shown in FIG. 3(d), when the respective liquid surfaces reach a position above the hole H, a lipid bilayer membrane 23 having a thickness of about 50 Angstrom will be formed over the hole H.

In this embodiment, the lipid bilayer membrane is produced by the folding method. But this invention should by no means be limited to the illustrated method; For example, the painting method (described in, for example, "Bilayer Lipid Membranes, Theory and Practice" by H. Tien and Ti, published by Mancel Dekker 1974), in which lipid dissolved in an organic solvent is painted over a membrane forming hole can also be utilized.

In the fourth step, as shown in FIGS. 3(e) and 3(f), an ion pump 23p and an ion channel are reconstituted in the lipid bilayer membrane 23. At that time, protein is used in a solubilized form, by a surfactant active, and polypeptide is used as an ethanol solution. In this embodiment, an ethanol solution of the ion pump or ion channel solubilized by a method described below is added to the buffer so that the ion channel or ion pump is spontaneously reconstituted into the lipid bilayer membrane. The ion pump and ion channel should comprise bacteriorhodopsin (bR, proton pump: regarding the purification, see, for example, Japanese Patent Laid-Open Publication No. Hei 2-247894) and gramicidin (cation channel: see, for example, "Annual Review of Physiology" by O. S. Adersen, 46, 1984).

For solubilizing bR, which is to be the ion pump 23p, a purple membrane is solubilized by a surfactant solution, such as a sodium acetate aqueous solution of 1 mol/l including 5% triton X-100, and then substituted by surfactant such as with octyglucosid (OG) or deoxycholic acid (DOC) (see, for example, "Methods in Enzymology" by H. Bayley et al., vol. 88, 74–81, 1982). This solubilized bR is added to the buffer solution 22 in the compartment X or compartment Y to be spontaneously reconstituted into the lipid bilayer membrane 13 to form an ion pump 23p. At that time, several tens of $\mu$gs of solubilized bR should be added to the buffer.

In the embodiment, gramicidin, which is to be an ion channel, is added as an ethanol solution is added to the buffer 22 in both the compartment X and the compartment Y so as to be similarly reconstituted into the lipid bilayer membrane 23. At that time, in this embodiment, the gramicidin-ethanol solution is added to the compartment, to which the bR was not added, in such a manner that the concentration of gramicidin in the buffer 22 of the cell 21 becomes several tens of pmol/l.

In this embodiment, bR is used as the ion pump. Alternatively, the ion pump may be halorhodopsin (hR: regarding the purification, see, for example, "Biological Chemistry" by A. Duschl et al., 263, 32, 1988), which transports chloride ions in response to light irradiation, or ATPase (see, for example, "Biochem. Biophys. Acta" by E Muneyuki et al., 1058, 1991), which transports protons as well as cations, such as sodium ions, potassium ions or calcium ions by consuming a substrate added to the solution.

Also, the ion channel may be a voltage-dependent ion channel exemplified by gramicidin as well as melittin (anion channel: see, for example, "Biochim. Biophys. Acta" by C. E. Dempsey, 1031, 1990) and alamethicin (cation: see, for example, "Biochim. Biophys. Acta" by L. G. M. Gordon and D. A. Haydon, 436, 1976). Out of these ion channels, one selectively allowing the ions with a polarity which corresponds to that of the ions to be transported by the ion pump to pass through should be used.

[Generation of Oscillating Electrical Signal]

FIGS. 4(a) through 4(d) show the mode of operation of this embodiment. FIGS. 5(a) and 5(b) show variation of the membrane potential difference (ion concentration difference) according to computer simulation conducted under the conditions of this embodiment.

Figure 4:
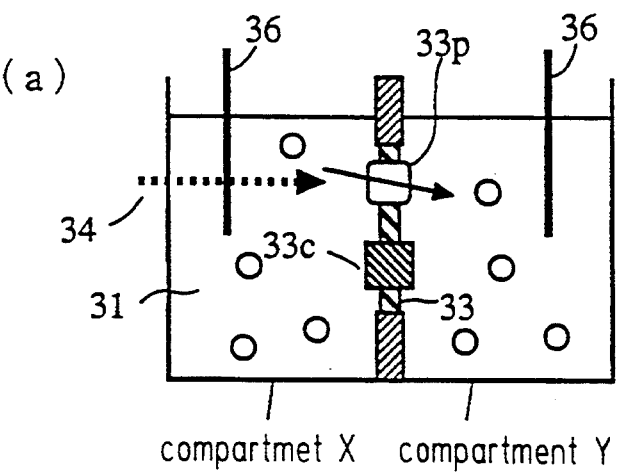
FIGS. 4(a) through 4(d) are diagrams showing the modes of operation of the neural modeling device of the first embodiment.
Figure 4:
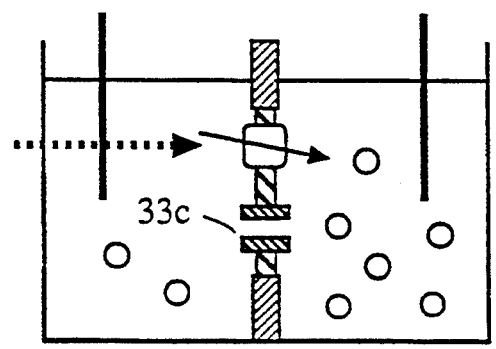
Figure 4:
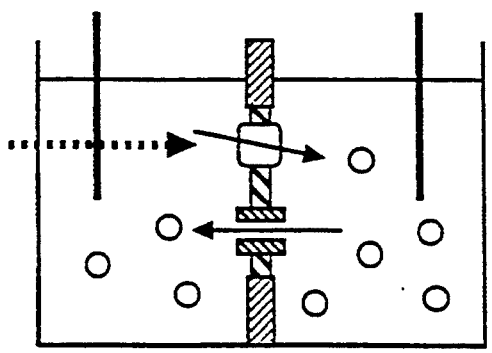
Figure 4:
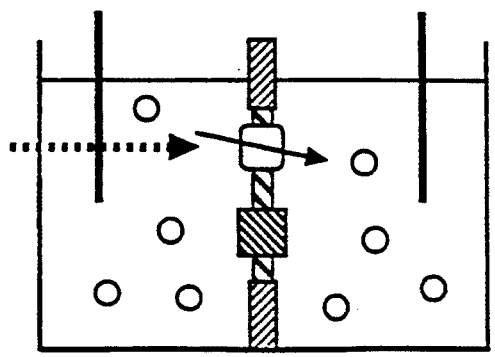
Figure 5:
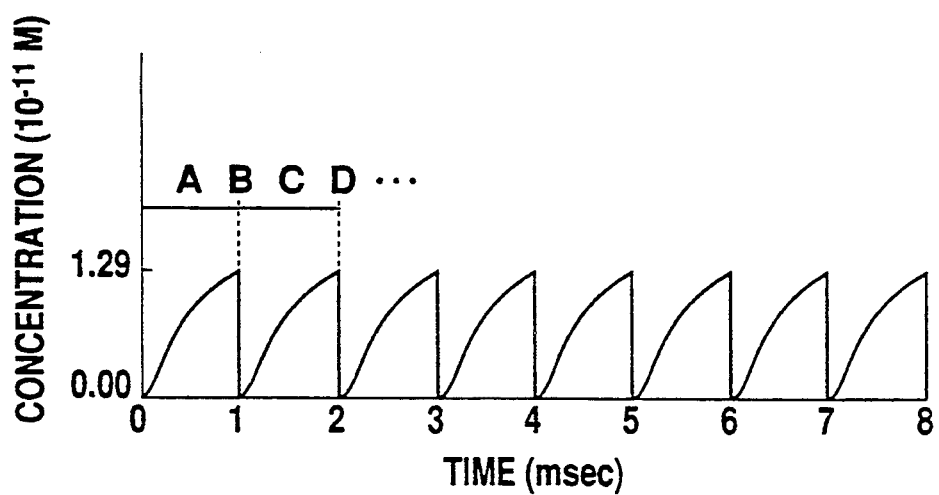
FIGS. 5(a) and 5(b) show oscillating electrical signals to be obtained by the neural modeling device of the first embodiment.
Figure 5:
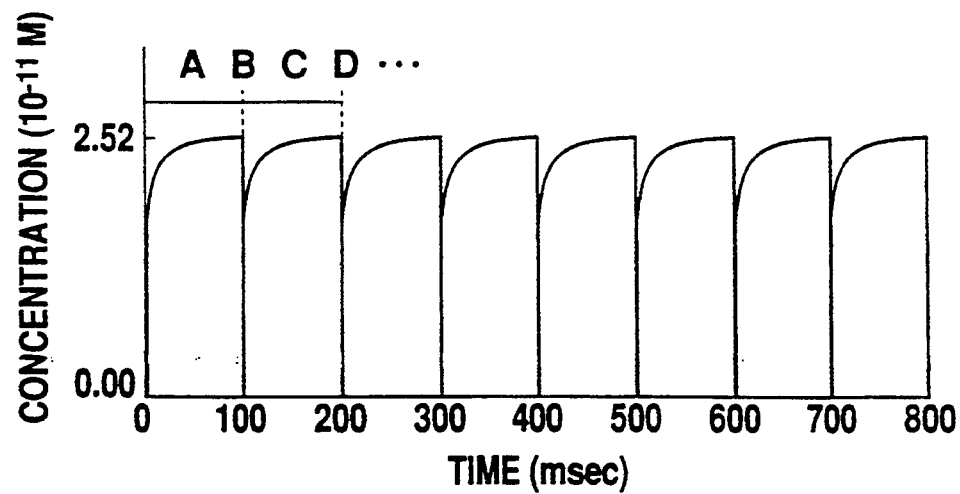

The first step (FIG. 4(a)): an ion pump 33p buried in a lipid bilayer membrane 33 transports selected ions (o) through the lipid bilayer membrane 33 from one side (compartment X) to the other side (compartment Y) of an electrolyte 31 in response to an external stimulus, such as light irradiation 34, to cause a difference in concentration of the selected ions (o) on opposite sides of the lipid bilayer membrane 33, thus leading to the increment of membrane potential difference (FIG. 5(a)).

The second step (FIG. 4(b)): an ion channel 33c likewise buried in the lipid bilayer membrane 33 opens, when the membrane potential difference reaches a threshold, to allow the selected ions (o), which are transported by the ion pump 33p, or those of the same sign to pass in the direction (from compartment Y to compartment X) of reducing the concentration difference.

The third step (FIG. 4(c)): at that time, since a quantity of the selected ions (o) to pass in a specified unit time is greater than that to be transported in the unit time by the ion pump 33p, the membrane potential difference will be reduced along with the passage of selected ions (o) through the channel (FIG. 5(b)), and hence the ion channel 33c will finally be closed.

The fourth step (FIG. 4(d)): since the ion pump 33p continues transporting the selected ions (o) in one direction in response to an external stimulus such as light irradiation 34, a difference in concentration of the selected ions (o) between opposite sides of the lipid bilayer membrane 33 is caused, which increases the membrane potential difference (FIG. 5(c)) so that the ion channel 33c opens. Then this step returns to the second step (FIG. 5(d)).

As the foregoing steps are repeated, it is possible to obtain a phenomenon in which the membrane potential difference fluctuates with a predetermined period, as an oscillating electrical signal from the electrode. FIG. 5(a) shows the difference in ion concentration of the ionic solution 32 between the compartment X and compartment Y, corresponding to the threshold at which the ion channel 33c opens, as it changes with time if the threshold is set at $3 \times 10^{-11}$ mol/l. FIG. 5(b) shows the ion concentration difference as it changes with time if the threshold is set at $2.5 \times 10^{-11}$ mol/l. The pattern of the vibrating signal depends on the ability of the ion pump and ion channel; that is, the vibrating signal changes in various ways according to the functions of protein and polypeptide situated in the lipid membrane.

Thus the oscillating electrical signal representing the phenomenon, in which the membrane potential difference obtained by the movement of the selected ions through the lipid membrane containing protein or polypeptide fluctuates, is fairly similar to the vibration phenomenon of membrane within living organisms both in structure and function.

With the neural modeling device of this invention, since it is able to control the ion transportation ability of the ion pump by an external stimulus (such as by light irradiation or substrate addition), an oscillating electrical signal having an optional vibration mode corresponding to the external stimulus can be obtained.

Second Embodiment

Figure 6:
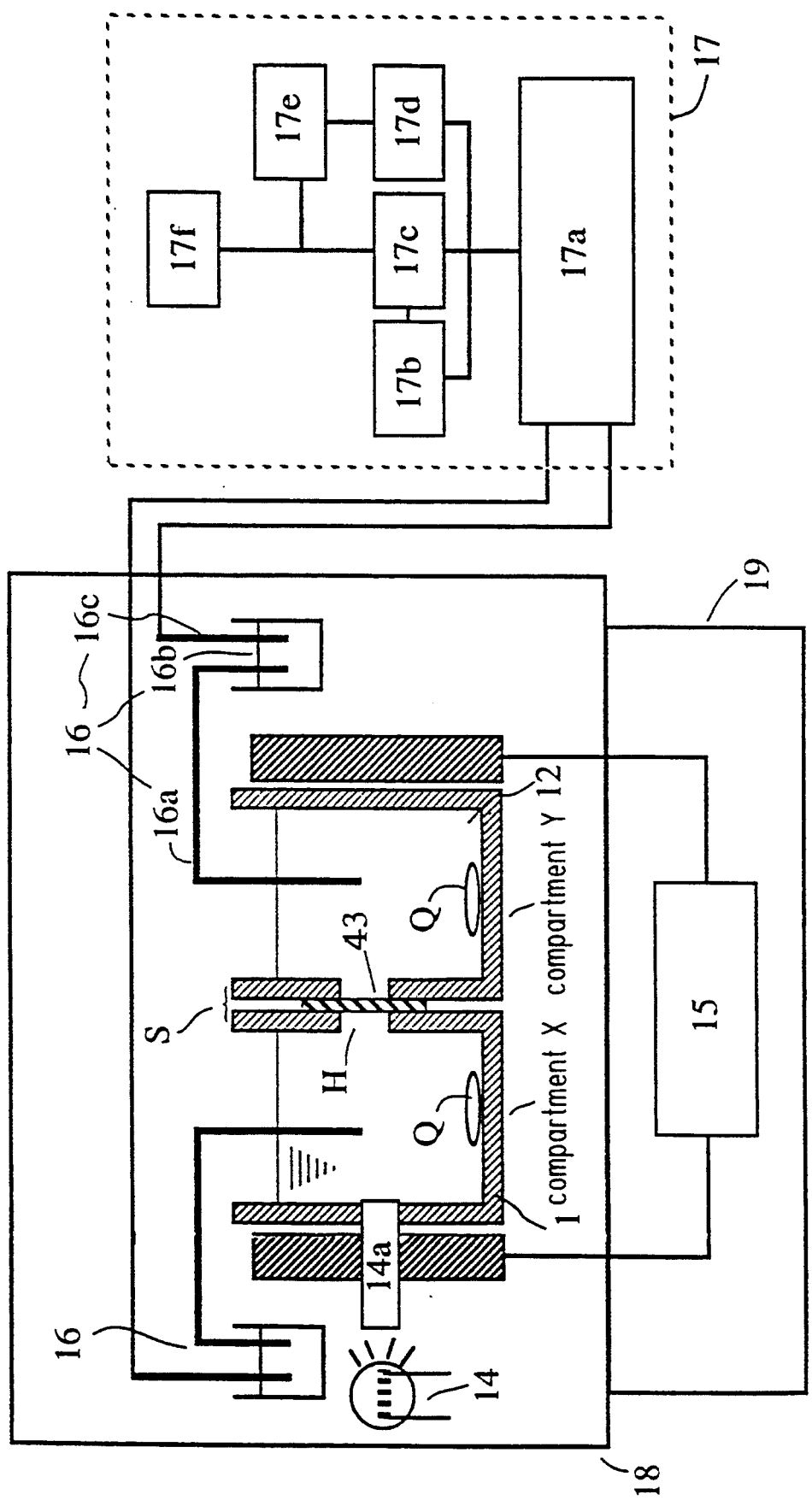
FIG. 6 is a diagram showing a membrane potential measuring system in the form of a neural modeling device according to a second embodiment of the invention.

FIG. 6 shows a membrane potential measuring system in the form of a neural modeling device according to a second embodiment of this invention.

As shown in FIG. 6, this neural modeling device, like that of the second embodiment, is formed by partioning a fluorocarbon polymer cell by a lipid-impregnated membrane 43 and by putting electrodes in the respective partitioned cells. In the lipid-impregnated membrane 43, an ion pump and an ion channel are buried. The parts or elements similar to those of the second embodiment are designated by like reference numerals; therefore their detailed description is omitted here for clarity.

The neural modeling device of the second embodiment is characterized by using a lipid-impregnated membrane 43 instead of the lipid bilayer membrane 13. The second embodiment is identical with the first embodiment in basic construction except the lipid-impregnated membrane 43; therefore, any repetition is omitted from the following description. In FIG. 6, for better understanding, the lipid-impregnated membrane 43 is shown to be the same in size and thickness as those of the lipid bilayer membrane 13 of the first embodiment shown in FIG. 2; however, they are actually different from each other both in size and thickness.

[Preparation of Lipid-impregnated Membrane]

A "lipid-impregnated membrane" is a membrane in which lipid is impregnated and is prepared by soaking a lipid-impregnatable membrane in lipid solution. Generally, the lipid-impregnatable membrane should be a porous membrane. In the second embodiment, a porous membrane (0.1 μm in pore diameter, about 0.15 mm in thickness) having a diameter of 10 mm or more was soaked in an n-decane solution containing azolectin of 200 mg/ml for several seconds. This lipid-impregnated membrane is characterized by its easy-preparation and stability compared with the bilayer lipid membrane. The material of this porous membrane is exemplified by cellulose, nitrocellulose, cellulose ester such as triacetylcellulose, and polytetrafluoroethylene.

[Production of Neural Modeling Device using Lipid-impregnated Membrane]

Figure 7:
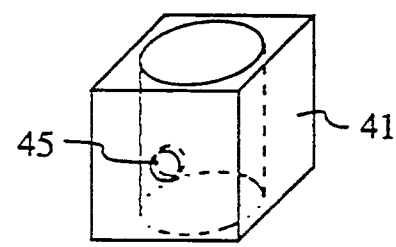
FIGS. 7(a), 7(b) and 7(c) show various steps of a method of manufacturing the neural modeling device of the second embodiment using a lipid-impregnated membrane.
Figure 7:
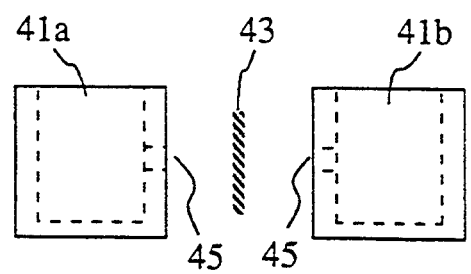
Figure 7:
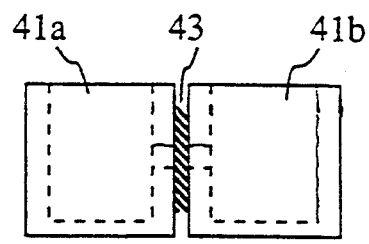

FIGS. 7(a), 7(b) and 7(c) show various steps in which the neural modeling device of the second embodiment is produced.

The neural modeling device of the second embodiment was prepared by sandwiching the lipid-impregnated membrane 43 between two cells 41a, 41b of fluoric resin. Each cell is a hollow cube of 1.5 cc volume, with uppermost faces open, and a side surface of each cube which meets the other cube has a hole 45 having a diameter of 7.8 mm. Because of this sandwiched structure, the two compartments are partitioned by the lipid-impregnated membrane.

[Method of Ion Pump Reconstitution]

In burying the ion pump, a solution containing the ion pump was injected into one of the two cells to be absorbed to the lipid-impregnated membrane. In this embodiment, a purple membrane was used as the ion pump.

The purple membrane was buried by the conventional method exemplified by "Analytical Biochemistry" by L. A. Brachev et al., 96, 1979, pp. 250–262 and "FEBS Letters" by M. C. Block et al., 76 (1), 1977, pp. 45–50.

In the second embodiment, the solution containing the ion pump was prepared by dissolving 1.5 mg of purple membrane in 1.0 ml of water. The ion pump (purple membrane) was buried in the lipid-impregnated membrane by about one-hour stirring after injecting about 80 μl of above purple membrane solution.

Alternatively, in this ion pump burying method, a piece of purple membrane itself or solubilized bacteriorhodopsin may be added, or these may be used in the form reconstituted into liposome.

Since the ion pump is activated by light, the light source 14 should be situated on the side at which the ion pump is buried. Since the membrane is transparent to some degree, the light may be irradiated from the other side. However, in this case, the efficiency is reduced.

[Method of Burying Ion Channel]

Both cells 41a and 41b have been filled with the water beforehand. In burying the ion channel, an ethanol solution containing 20 μg of alamethicin as the ion channel was provided by adding 20 ml of 1 mg of alamethicin/l solution.

The lipid, ion pump and ion channel may be alternative substances.

[Measurement of Oscillation of Neural Modeling Device]

Figure 8:
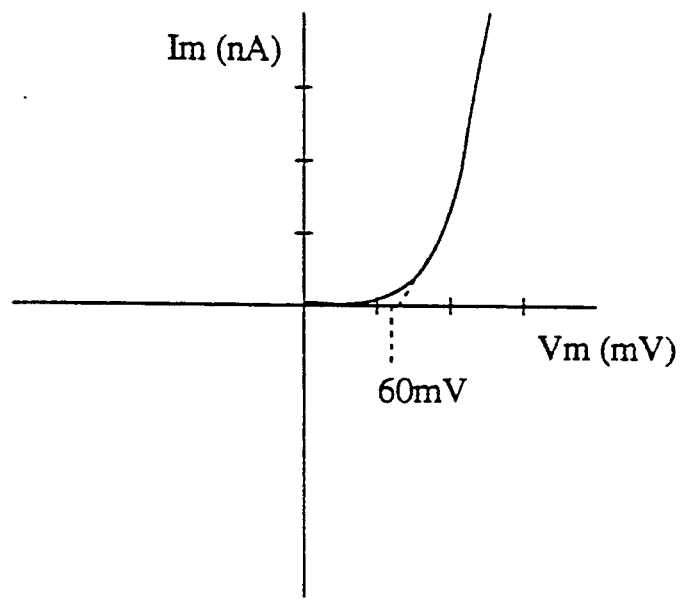
FIG. 8 is a graph showing an I-V curve of alamethicin (alamethicin-added side is positive)

FIG. 8 shows ("Membrane Biology" by G. Andrew et al., 129, 1992, pp. 109–136) showing an I–V characteristic of alamethicin (the side at which alamethicin is to be added is positive).

Figure 9:
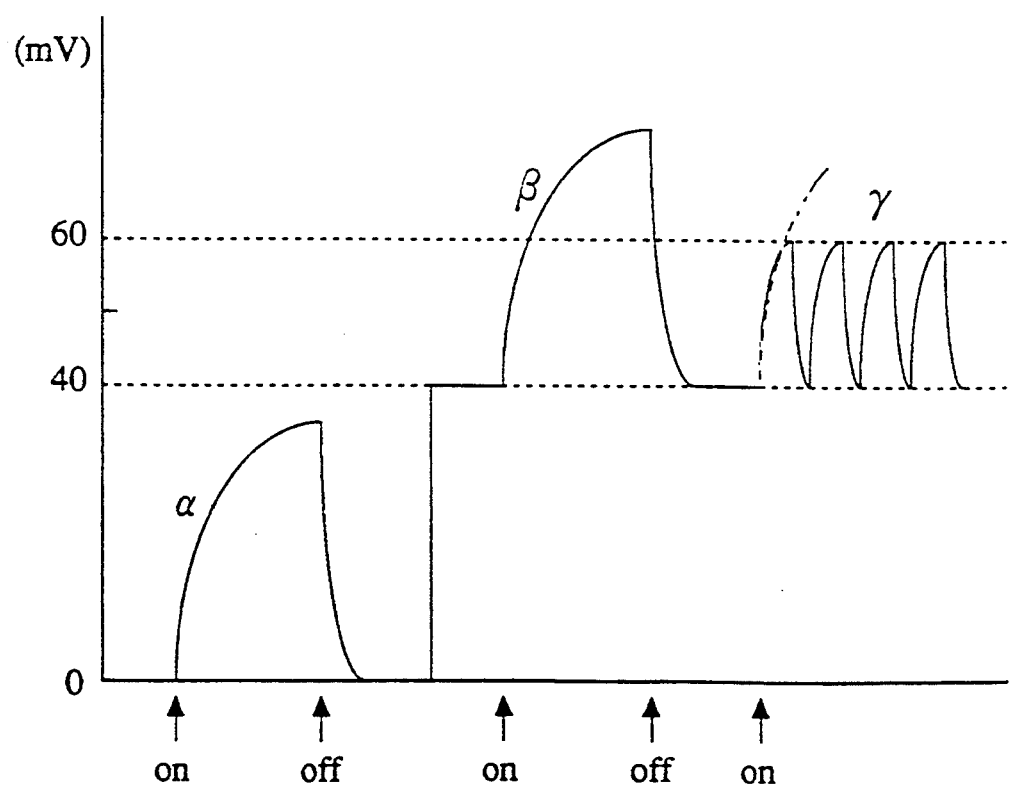
FIG. 9 shows an oscillating electrical signal to be obtained by the neural modeling device of the second embodiment, where $a$ is a light response in the absence of alamethicin (purple membrane), $\beta$ is a light response when a base voltage at the II side is increased up to 40 mV, and c is a light response when alamethicin is added to the II side.

FIG. 9 shows an oscillating electrical signal obtained by the neural modeling device of the second embodiment. In FIG. 9, a is a light response in the absence of alamethicin (purple membrane), b is a light response when the base voltage at a side 41b was increased to 40 mV, and c is a light response when alamethicin was added.

It turns out from FIG. 8 that in the presence of alamethicin, the degree of electrical conduction is increased sharply around 60 mV. When the base voltage was increased in such a manner that the membrane potential to be caused by the action of the ion pump (purple membrane) reached this value, a vibration such as indicated by c in FIG. 9 was obtained.

According to this invention, by combining the ion pump, which is buried in the lipid or lipid-impregnated membrane so as to divide the electrolyte and which serves to increase the membrane potential difference by the ion transportation in response to an external stimulus, with the ion channel, which opens, depending on this membrane potential difference, to reduce the potential difference, it is possible to obtain a phenomenon in which the membrane potential difference fluctuates with a constant period, and hence it is possible to obtain an oscillating electrical signal situated at opposite sides of the lipid membrane, having a vibration mode corresponding to an external stimulus such as optical stimulus. This signal is a vibration element to be the nucleus of a bio-information processing system and hence can be the base of a biocomputer.

What is claimed is:

1. A neural modeling device for generating an oscillating electrical signal, comprising:
   (a) a container;
   (b) a lipid membrane situated so as to divide said container into two compartments;
   (c) an electrolyte in each compartment, the electrolyte in each compartment being at a potential;
   (d) electrodes contacting the electrolyte in each compartment for transmitting the potentials of the electrolyte as an electrical signal;
   (e) an ion pump buried in said lipid membrane being capable of active-transport of ions in said electrolyte through said lipid membrane from one side to the other side in response to an external stimulus; and
   (f) an ion channel buried in said electrolyte being capable of passive-transport of ions of the same sign as that of the ions actively transported by said ion pump.

2. A neural modeling device according to claim 1, wherein said ion pump is bacteriorhodopsin.

3. A neural modeling device according to claim 1 wherein transport of ions by said ion pump creates a potential difference between said two compartments and said ion channel is capable of beginning transport of ions only when the potential difference reaches a threshold.

4. A neural modeling device according to claim 3 wherein said ion channel transports ions through said lipid membrane from the other side to the one side.

5. A neural modeling device according to claim 4 wherein the ion pump and the ion channel transport ions of the same type.

6. A neural modeling device for generating an oscillating electrical signal, comprising:
   (a) a container;
   (b) a lipid-impregnated membrane situated so as to divide said container into two compartments;
   (c) an electrolyte in each compartment, the electrolyte in each compartment being at a potential;
   (d) electrodes contacting the electrolyte in each compartment for transmitting the potentials of the electrolyte as an electrical signal;
   (e) an ion pump buried in said lipid-impregnated membrane being capable of active-transport of ions in said electrolyte through said lipid-impregnated membrane from one side to the other side as a result of an external stimulus; and (f) an ion channel buried in said lipid-impregnated membrane being capable of passive-transport of ions of the same sign as that of the ions actively transported by said ion pump.

7. neural modeling device according to claim 6, wherein said ion pump is bacteriorhodopsin.

8. A neural modeling device according to claim 6 wherein transport of ions by said ion pump creates a potential difference between said two compartments and said ion channel is capable of beginning transport of ions only when the potential difference reaches a threshold.

9. A neural modeling device according to claim 8 wherein said ion channel transports ions through said lipid membrane from the other side to the one side.

10. A neural modeling device according to claim 9 wherein the ion pump and the ion channel transport ions of the same type.

* * * * *